(12) United States Patent
Trevethick et al.

(10) Patent No.: US 8,178,330 B2
(45) Date of Patent: May 15, 2012

(54) FERMENTATION OF GASEOUS SUBSTRATES

(75) Inventors: Simon Richard Trevethick, Auckland (NZ); Jason Carl Bromley, Auckland (NZ); Sean Dennis Simpson, Auckland (NZ); Vinod Khosla, Auckland (NZ)

(73) Assignee: Lanza Tech New Zealand Limited, Auckland (NZ)

( * ) Notice: Subject to any disclaimer, the term of this patent is extended or adjusted under 35 U.S.C. 154(b) by 0 days.

(21) Appl. No.: 13/058,727

(22) PCT Filed: Sep. 3, 2010

(86) PCT No.: PCT/NZ2010/000176
§ 371 (c)(1),
(2), (4) Date: Jun. 28, 2011

(87) PCT Pub. No.: WO2011/028137
PCT Pub. Date: Mar. 10, 2011

(65) Prior Publication Data
US 2011/0244538 A1 Oct. 6, 2011

Related U.S. Application Data

(60) Provisional application No. 61/240,237, filed on Sep. 6, 2009, provisional application No. 61/332,142, filed on May 6, 2010.

(51) Int. Cl.
*C12P 7/06* (2006.01)
(52) U.S. Cl. .................................................. 435/161
(58) Field of Classification Search .................. 435/161
See application file for complete search history.

(56) References Cited

U.S. PATENT DOCUMENTS

| | | | |
|---|---|---|---|
| 5,173,429 A | 12/1992 | Gaddy et al. | |
| 5,312,567 A | 5/1994 | Kozma et al. | |
| 5,593,886 A | 1/1997 | Gaddy | |
| 5,807,722 A | 9/1998 | Gaddy | |
| 5,821,111 A | 10/1998 | Grady et al. | |
| 6,136,577 A | 10/2000 | Gaddy | |
| 6,340,581 B1 | 1/2002 | Gaddy | |
| 6,368,819 B1 | 4/2002 | Gaddy et al. | |
| 6,551,805 B2 * | 4/2003 | Ho et al. | 435/132 |
| 6,753,170 B2 | 6/2004 | Gaddy et al. | |
| RE39,175 E | 7/2006 | Gaddy et al. | |
| 7,196,218 B2 | 3/2007 | Gaddy et al. | |
| 7,285,402 B2 | 10/2007 | Gaddy et al. | |
| 2003/0147791 A1 | 8/2003 | Ding et al. | |
| 2007/0275447 A1 | 11/2007 | Lewis et al. | |
| 2010/0323417 A1 | 12/2010 | Simpson et al. | |

FOREIGN PATENT DOCUMENTS

| | | |
|---|---|---|
| WO | 2008/028055 | 3/2008 |
| WO | 2008/154301 | 12/2008 |
| WO | 2009/020747 | 2/2009 |

OTHER PUBLICATIONS

Bledwell et al. 1999; Reactor design issues for synthesis-gas fermentation. Biotechnology progress 15(5): 834-844.*
Sulzer Chemtech, 2010 at www.sulzerchemtech.com/portaldata/11/Resources//brochures/mtt/Structured_Packings_April_2010.pdf.*
Jianxi Runda Petrochemical Technology Services, Co. 1999; at www.newmaker.com/productdetail/104720/mellapak-ceramic-structred-packings.html.*
Phillips, J.R., et al. "Synthesis Gas as Substrate for the Biological Production of Fuels and Chemicals." Applied Biochemistry and Biotechnology, 1994, 45/46. pp. 145-157.
Abrini J. et al. "*Clostridium* autoethanogenum, sp. Nov., an Anaerobic Bacterium that Produces Ethanol from Carbon Monoxide", Archives of Microbiology. 1994, vol. 161, pp. 345-351.
Ragsdale, S.W. "Life with Carbon Monoxide." Critical Reviews in Biochemistry and Molecular Biology, 2004, 39, pp. 165-195.
Henstra, et al. "Microbiology of Synthesis Gas Fermentation for Biofuel Production." Current Opinion in Biotechnology, 2007, 18, pp. 200-206.

* cited by examiner

*Primary Examiner* — Karen Carlson
(74) *Attorney, Agent, or Firm* — Frank S Molinaro (57) ABSTRACT

The invention relates to the microbial fermentation of gaseous substrates, particularly to gas/liquid contact modules and bioreactors configured to improve the efficiency of fermentations, particularly microbial fermentations of substrates comprising CO. In a particular embodiment, a gas/liquid contact module with multiple channels is configured to produce products in a liquid fermentation broth. In a further particular embodiment, there is provided a method of fermentation of a gaseous substrate to produce a product in a liquid fermentation broth.

20 Claims, 5 Drawing Sheets

FERMENTATION OF GASEOUS SUBSTRATES

CROSS REFERENCE TO RELATED APPLICATIONS

This application is a National Stage of International Application No. PCT/NZ2010/000176, filed on Sep. 3, 2010, which claims priority to the following US Provisional Applications: U.S. Provisional Application No. 61/240,237 filed Sep. 6, 2009 and U.S. Provisional Application 61/332,142 filed May 6, 2010. The contents of the prior applications mentioned above are incorporated herein by reference.

FIELD OF THE INVENTION

The invention relates to the microbial fermentation of gaseous substrates. In particular, the invention relates to gas/liquid contact modules and bioreactors configured to improve the efficiency of fermentations, particularly microbial fermentations of substrates comprising CO.

BACKGROUND OF THE INVENTION

Ethanol is rapidly becoming a major hydrogen-rich liquid transport fuel around the world. Worldwide consumption of ethanol in 2005 was an estimated 12.2 billion gallons. The global market for the fuel ethanol industry has also been predicted to grow sharply in future, due to an increased interest in ethanol in Europe, Japan, the USA, and several developing nations.

For example, in the USA, ethanol is used to produce E10, a 10% mixture of ethanol in gasoline. In E10 blends the ethanol component acts as an oxygenating agent, improving the efficiency of combustion and reducing the production of air pollutants. In Brazil, ethanol satisfies approximately 30% of the transport fuel demand, as both an oxygenating agent blended in gasoline, and as a pure fuel in its own right. Also, in Europe, environmental concerns surrounding the consequences of Green House Gas (GHG) emissions have been the stimulus for the European Union (EU) to set member nations a mandated target for the consumption of sustainable transport fuels such as biomass derived ethanol.

The vast majority of fuel ethanol is produced via traditional yeast-based fermentation processes that use crop derived carbohydrates, such as sucrose extracted from sugarcane or starch extracted from grain crops, as the main carbon source. However, the cost of these carbohydrate feed stocks is influenced by their value as human food or animal feed, while the cultivation of starch or sucrose-producing crops for ethanol production is not economically sustainable in all geographies. Therefore, it is of interest to develop technologies to convert lower cost and/or more abundant carbon resources into fuel ethanol.

CO is a major, low cost, energy-rich by-product of the incomplete combustion of organic materials such as coal or oil and oil derived products. For example, the steel industry in Australia is reported to produce and release into the atmosphere over 500,000 tonnes of CO annually. Additionally or alternatively, CO rich gas streams (syngas) can be produced by gasification of carbonaceous materials, such as coal, petroleum and biomass. Carbonaceous materials can be converted into gas products including CO, CO2, H2 and lesser amounts of CH4 by gasification using a variety of methods, including pyrolysis, tar cracking and char gasification. Syngas can also be produced in a steam reformation process, such as the steam reformation of methane or natural gas.

Catalytic processes may be used to convert gases consisting primarily of CO and/or CO and hydrogen ($H_2$) into a variety of fuels and chemicals. Micro-organisms may also be used to convert these gases into fuels and chemicals. These biological processes, although generally slower than chemical reactions, have several advantages over catalytic processes, including higher specificity, higher yields, lower energy costs and greater resistance to poisoning.

The ability of micro-organisms to grow on CO as a sole carbon source was first discovered in 1903. This was later determined to be a property of organisms that use the acetyl coenzyme A (acetyl CoA) biochemical pathway of autotrophic growth (also known as the Woods-Ljungdahl pathway and the carbon monoxide dehydrogenase/acetyl CoA synthase (CODH/ACS) pathway). A large number of anaerobic organisms including carboxydotrophic, photosynthetic, methanogenic and acetogenic organisms have been shown to metabolize CO to various end products, namely $CO_2$, $H_2$, methane, n-butanol, acetate and ethanol. While using CO as the sole carbon source, all such organisms produce at least two of these end products.

Anaerobic bacteria, such as those from the genus *Clostridium*, have been demonstrated to produce ethanol from CO, $CO_2$ and $H_2$ via the acetyl CoA biochemical pathway. For example, various strains of *Clostridium ljungdahlii* that produce ethanol from gases are described in WO 00/68407, EP 117309, U.S. Pat. Nos. 5,173,429, 5,593,886, and 6,368,819, WO 98/00558 and WO 02/08438. The bacterium *Clostridium autoethanogenum* sp is also known to produce ethanol from gases (Abrini et al., Archives of Microbiology 161, pp 345-351 (1994)).

However, ethanol production by micro-organisms by fermentation of gases is typically associated with co-production of acetate and/or acetic acid. As some of the available carbon is typically converted into acetate/acetic acid rather than ethanol, the efficiency of production of ethanol using such fermentation processes may be less than desirable. Also, unless the acetate/acetic acid by-product can be used for some other purpose, it may pose a waste disposal problem. Acetate/acetic acid is converted to methane by micro-organisms and therefore has the potential to contribute to GHG emissions.

WO2007/117157, WO2008/115080 and WO2009/022925, the disclosure of which are incorporated herein by reference, describe processes that produce alcohols, particularly ethanol, by anaerobic fermentation of gases containing carbon monoxide. WO2007/117157, describes a process that produces alcohols, particularly ethanol, by anaerobic fermentation of gases containing carbon monoxide. Acetate produced as a by-product of the fermentation process is converted into hydrogen gas and carbon dioxide gas, either or both of which may be used in the anaerobic fermentation process. WO2008/115080, describes a process for the production of alcohol(s) in multiple fermentation stages. By-products produced as a result of anaerobic fermentation of gas(es) in a first bioreactor can be used to produce products in a second bioreactor. Furthermore, by-products of the second fermentation stage can be recycled to the first bioreactor to produce products. WO2009/022925 discloses the effect of pH and ORP in the conversion of substrates comprising CO to products such as acids and alcohols by fermentation.

Fermentation of gaseous substrates can be challenging due to the requirement that at least a portion of the gaseous substrate is dissolved in a typically aqueous fermentation broth before the substrate can be metabolised by a microbial culture. Fermentations involving gaseous substrates, wherein one or more gaseous components are the carbon and optionally the energy source for a microorganism, are particularly challenging due to the large amount of substrate required to be solubilised in a fermentation broth before any metabolism can take place. Examples of gaseous substrates used as a carbon and/or energy source in fermentation include CO, $CO_2$, $CH_4$, $H_2$ and $H_2S$. In particular, sparingly soluble substrates, such as CO and/or $H_2$ require highly efficient mass transfer into an aqueous fermentation broth as CO is both a carbon and energy source for anaerobic fermentation. For example, the theoretical equations for CO and $H_2$ to ethanol are:

Thus, six molecules of gas (CO and/or $H_2$) must be dissolved in a fermentation broth to produce one molecule of ethanol.

Mass transfer of a gas into a liquid is a function of three main variables:

1. Concentration Driving Force: The partial pressure of a particular gaseous component is substantially proportional to the rate at which that component can be driven into a solution.
2. Interfacial Surface Area: The larger the interfacial surface area between gas and liquid phases, the higher the opportunity for mass transfer. In particular, the interfacial surface area is typically a function of gas hold-up and bubble size.
3. Transfer Coefficient: The transfer coefficient of a system is influenced by a variety of factors. However, from a practical perspective, typically the largest influence is the relative velocity between the liquid and the gas phases. Relative velocities (and hence mass transfer) are typically increased by increasing turbulence through agitation or other mixing.

Many devices and equipment for promotion of mass transfer to microorganisms in fermentation of gaseous substrates are known. However, they typically require large amounts of energy in order to attain the necessary mass transfer rates. For example, in order to achieve effective fermentation of CO and optionally $H_2$ into products, such as acid(s) and alcohol(s), the substrate must be made available to the microorganisms in an efficient manner. This is typically achieved by increasing mass transfer rates of CO and optionally $H_2$ molecules into solution by mechanical means, such as vigorous stirring. These methods for increasing mass transfer require a large power input, which becomes inefficient and/or uneconomical as scale increases.

It is an object of the present invention to provide system(s) and/or method(s) that overcomes disadvantages known in the art and provides the public with new methods for the optimal production of a variety of useful products.

SUMMARY OF THE INVENTION

According to a first aspect, there is provided a bioreactor system for fermentation of a gaseous substrate comprising CO and optionally $H_2$, or $CO_2$ and $H_2$, to one or more products, the system including:
 (a) at least one fermentation vessel, configured such that in use, liquid fermentation broth can be circulated in a loop;
 (b) at least one pumping means, configured to, in use, circulate fermentation broth and optionally the gaseous substrate gas around the loop;
 (c) at least one gas inlet configured to, in use, direct gaseous substrate into the vessel; and
 (d) at least one gas outlet, configured to, in use, allow gas to exit the vessel.

According to a second aspect, there is provided a gas/liquid contact module configured for fermentation of gaseous substrates, wherein the contact module comprises multiple channels.

In particular embodiment, one or more contact modules are included in a bioreactor.

According to a third aspect, the invention provides a bioreactor for fermentation of a gaseous substrate compromising one or more gas/liquid contact modules comprising multiple channels.

In particular embodiments of the first and second aspects, the bioreactor is configured for fermentation of a gaseous substrate to produce products including acid(s) and/or alcohol(s). In particular embodiments, the gaseous substrate comprises CO and optionally $H_2$.

In particular embodiments, the contact module is configured to provide effective mass transfer of the gaseous substrate to one or more micro-organisms in a liquid nutrient media.

In certain embodiments, the contact module is configured such that, in use, a gaseous substrate and a liquid nutrient media pass through the channels. According to particular embodiments, the channels are configured such that Taylor flow of the gaseous substrate and the liquid nutrient media occurs. Typically, Taylor flow is promoted where the channels have a cross-sectional diameter of 1-5 mm.

In particular embodiments, the contact module is constructed of ceramic material such as cordierite, porcelain, mullite or alumina, wherein the channels are separated by substantially solid walls of the ceramic material. In another embodiment, the contact module is constructed of resiliently flexible corrugated sheets laid and/or rolled such that multiple channels run the length of the module. Such modules are typically constructed of metal, such as stainless steel foil or plastic material.

The channels in the contact module can have diameters ranging from millimeters to tens of centimeters, however, Taylor flow in aqueous systems occurs in channels of approx 1-5 mm. The rate at which the liquid nutrient media and gaseous substrate move through the contact module will be dependent on the cross-sectional area of the channels. As such, the channel density will have a significant influence on power input. In particular embodiments, the channel density is at least 100 channels per square inch (cpsi); or at least 200 cpsi; or at least 300 cspi; or at least 400 cspi; or at least 500 cspi.

In particular embodiments, the bioreactor is used for the fermentation of gaseous substrates comprising CO and optionally $H_2$ to produce products including alcohols such as ethanol. Typically, the microbial fermentation of such substrates is carried out in aqueous liquid nutrient media by carboxydotrophic bacteria, such as *Clostridium autoethanogenum*. In particular embodiments, the fermentation is conducted by micro-organisms suspended in the liquid nutrient media. However, in particular embodiments, the micro-organisms can form a biofilm on the contact module, particularly in the channels of the contact module.

According to a fourth aspect, there is provided a method of improving efficiency of mass transfer of a gaseous substrate to one or more micro-organisms in a liquid nutrient media, the method including passing the gaseous substrate and liquid nutrient media through a gas/liquid contact module comprising multiple channels.

According to a fifth aspect, there is provided a method of fermentation of gaseous substrates to produce products comprising:

(a) providing a gaseous substrate to a circulated liquid loop bioreactor containing a culture of one or more microorganisms; and
(b) fermenting the culture in the bioreactor to produce one or more products from said substrate.

According to a sixth aspect, there is provided a method of producing products including acids and/or alcohols by fermentation of a gaseous substrate comprising CO, the method including:
(a) providing the gaseous substrate comprising CO to a circulated liquid loop bioreactor containing a culture of one or more microorganisms; and
(b) anaerobically fermenting the culture in the bioreactor to produce one or more products including one or more acids and/or alcohols from said substrate.

In particular embodiments of the fourth and fifth aspects, the circulated loop bioreactor includes one or more liquid/gas contact portions. In particular embodiments, the liquid/gas contact portion is a liquid/gas contact module.

In particular embodiments of the third, fourth and fifth aspects, the contact module is as described in the first and second aspects. In particular embodiments, the method includes passing gaseous substrate and liquid nutrient media pass through the channels in Taylor flow.

In particular embodiments, the one or more micro-organisms produces products including acid(s) and alcohol(s) from CO and optionally H2 by anaerobic fermentation. In particular embodiments, the one or more microbial cultures convert CO and optionally H2 to products including acid(s) and/or alcohol(s). In certain embodiments, the product is ethanol.

In particular embodiments, the microbial culture is a culture of carboxydotrophic bacteria. In certain embodiments, the bacteria is selected from *Clostridium, Moorella* and *Carboxydothermus*. In particular embodiments, the bacterium is *Clostridium autoethanogenum*.

In particular embodiments of the invention, the microorganisms are suspended in the liquid nutrient media, which contains nutrients required for microbial growth and metabolite production. In another embodiment of the invention, the micro-organisms form a bio-film in the contact module.

According to various embodiments of the invention, the carbon source for the fermentation reaction is syngas derived from gasification. The syngas substrate will typically contain a major proportion of CO, such as at least about 20% to about 95% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume. Substrates having lower concentrations of CO, such as 6%, may also be appropriate, particularly when significant amounts of $H_2$ and optionally $CO_2$ are present.

Embodiments of the invention find particular application in the production of acids and alcohols, particularly ethanol by fermentation of a gaseous substrate comprising CO. The substrate may comprise a gas obtained as a by-product of an industrial process. In certain embodiments, the industrial process is selected from the group consisting of ferrous metal products manufacturing, non-ferrous products manufacturing, petroleum refining processes, gasification of biomass, gasification of coal, electric power production, carbon black production, ammonia production, methanol production and coke manufacturing. In one embodiment of the invention, the gaseous substrate is syngas. In one embodiment, the gaseous substrate comprises a gas obtained from a steel mill.

Such CO-containing substrates will typically contain a major proportion of CO, such as at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume. In some embodiments, the substrate stream comprises low concentrations of H2, for example, less than 5%, or less than 4%, or less than 3%, or less than 2%, or less than 1%, or is substantially hydrogen free.

In a seventh aspect of the invention, there is provided a bioreactor system for fermentation of a gaseous substrate to produce products, the system including:
(a) a fermentation vessel including a gas/liquid contact module comprising multiple channels; and
(b) means for introducing liquid nutrient media into the contact module; and
(c) means for introducing gaseous substrate into the contact module.

In particular embodiments, the fermentation vessel is configured such that fluid can be circulated through the vessel by gas. In particular embodiments, the fermentation vessel is a gas-lift bioreactor. In another embodiment, the fermentation vessel is configured such that fluid can be circulated through the vessel by liquid. In particular embodiments, the fermentation vessel is a liquid circulated loop bioreactor. Additionally or alternatively, the bioreactor is configured such that fluid is circulated through the vessel by gas and liquid.

In particular embodiments of the invention, the contact module is configured such that Taylor flow of the gaseous substrate and the liquid nutrient media is promoted through the channels.

In particular embodiments, the means for introducing liquid nutrient media and gaseous substrate are configured for concurrent flow of the substrate and media through the contact module. Alternatively, the introducing means are configured for countercurrent flow.

In particular embodiments of the invention, the system includes means for separating a gas/liquid mixture exiting the contact module.

In particular embodiments, the system includes recycling means for returning the separated gas and/or liquid back to the module.

Although the invention is broadly as defined above, it is not limited thereto and also includes embodiments of which the following description provides examples.

BRIEF DESCRIPTION OF THE DRAWINGS

The invention will now be described in detail with reference to the accompanying Figures in which.

DETAILED DESCRIPTION OF THE INVENTION

Efficient fermentation of gaseous substrates, such as gaseous substrates comprising CO, to produce products, such as acids and/or alcohols requires control of the amount of substrate transferred into a fermentation broth to ensure high rates of production of desired products and the prevention of inhibition. In addition, in order to maximise carbon capture, the amount of a substrate transferred into a fermentation broth, such that it can be converted into products by one or more micro-organisms, must be maintained at a high level. Furthermore, in order to maintain overall efficiency, the substrate should be transferred into solution such that power input across the system is minimised. In accordance with the invention, there is provided a fermentation system that surprisingly overcomes these challenges inherent in most known bioreactors. Thus, in particular embodiments, there is provided a bioreactor system for fermentation of a gaseous substrate comprising CO and optionally H2 to one or more products, the system including:
 (a) at least one fermentation vessel, configured such that in use, liquid fermentation broth can be circulated in a loop;
 (b) a pumping means, configured to, in use, circulate fermentation broth and optionally substrate gas around the loop;
 (c) a gas inlet configured to, in use, direct gaseous substrate into the vessel; and
 (d) a gas outlet, configured to, in use, allow gas to exit the vessel.

In particular embodiments, fermentation broth and optionally gaseous substrate is circulated around a closed loop by a pump wherein additional substrate is introduced via an inlet port. The transfer of the gaseous substrate into a typically aqueous fermentation broth (mass transfer) is effected by mixing the gas and liquid. In particular embodiments, the system includes at least one gas/liquid contact module in the closed loop, wherein gas and liquid are pushed through the contact module such that mixing occurs. The rate of mass transfer will be a function of gas/liquid interfacial surface area and transfer coefficient, which in accordance with the invention is a reflection of the rate at which gas bubbles and liquid move through the module. Up to a point, the faster liquid and gas can be pushed through the module, the higher the transfer coefficient and thus mass transfer rate. Thus, in accordance with particular embodiments of the invention, fermentation broth comprising one or more microorganisms is pumped through a vessel including at least one module. In such embodiments, mass transfer rate can be increased by increasing liquid and gas velocity in the module. For a given hold-up (gas-liquid ratio), increasing the gas/liquid slurry velocity through the module will increase the mass transfer coefficient.

In accordance with particular embodiments, the mass transfer rate of the gaseous substrate to the microbial culture can be controlled such that the microbial culture is supplied with substrate at or towards an optimum supply rate. In the bioreactors of the invention, the mass transfer rate can be controlled by controlling partial pressure of a desired compound (for example the proportion of CO supplied in a gas stream and/or the pressure of the gas stream) and/or by controlling the liquid flow-rate or gas holdup (via gas flow rate and/or the liquid flow rate).

In particular embodiments of the invention, the mass transfer rate can be controlled by controlling the rate at which fermentation broth is pumped through a vessel comprising one or more modules. In a particular embodiment, one or more modules are configured in a closed system forming a loop, wherein the liquid is pumped around the loop to drive mass transfer. Those skilled in the art will, upon consideration of the instant disclosure, recognise that the size and the geometry of the loop may be selected to achieve the desired substrate transfer and may be horizontally or vertically orientated, or a combination thereof.

The use of circulated liquid loop bioreactors for fermentation of gaseous substrates can overcome some of the limitations of known gas driven fermenter systems, such as mass transfer ceilings at excessive gas flows. For example, in gas driven systems, higher gas flows can cause a churn turbulent flow regime resulting in lower mass transfer efficiency. The successful utilisation of a circulated liquid loop bioreactor for fermentation of gaseous substrates to produce products is surprising for several reasons. Firstly, the fermentation broth is necessarily circulated by a pump, so the microorganisms need to be resistant or tolerant to shear. Secondly, gas/liquid mass transfer across the bioreactor is not necessarily homogeneous, leading to areas within the bioreactor of high mass transfer and areas of low mass transfer.

Thus, in accordance with a particular aspect of the invention, there is provided a method of fermentation of gaseous substrates to produce products comprising:
 (a) providing a gaseous substrate to a circulated liquid loop bioreactor containing a culture of one or more microorganisms; and
 (b) fermenting the culture in the bioreactor to produce one or more products from said substrate.

The use of the circulated liquid loop bioreactor is particularly effective in embodiments where control of mass transfer into a fermentation broth is important, as the mass transfer rate can be controlled by both gas supply rate and liquid recycle rate. Thus, in particular embodiments, there is provided a method of producing products including acids and/or alcohols by fermentation of a gaseous substrate comprising CO, the method including:
 (a) providing the gaseous substrate comprising CO to a circulated liquid loop bioreactor containing a culture of one or more microorganisms; and
 (b) anaerobically fermenting the culture in the bioreactor to produce one or more products including one or more acids and/or alcohols from said substrate.

In particular embodiments, such as the fermentation of CO to produce products, such as acid(s) and/or alcohol(s), waste gases, such as CO2 can be produced. In particular embodiments, gaseous waste and optionally gaseous components not converted to products need to pass out of the closed loop. Thus, in particular embodiments, the vessel includes disengagement means, wherein gaseous waste and optionally gaseous components not converted to products are able to disengage from the circulating fermentation broth, and exit the bioreactor. Upon consideration of the instant disclosure, those skilled in the art will recognise equipment or design geometry to control the amount of disengagement. In particular embodiments, there bioreactor includes a disengagement cavity above the fermentation broth, wherein gas disengages from the broth and can exit the bioreactor. In a non-coalescing gas-liquid system, higher gas retention will increase overall gas holdup and thus transfer rate, but may adversely affect pump performance. In the majority of designs, disengagement itself will also be a function of liquid flow rate and gas holdup.

In particular embodiments, a substantially constant gaseous substrate supply may mean that gas flow is not an adjustable variable to control mass transfer. Thus control over liquid pump speed and thus the amount of gaseous components entrained in the circulating fermentation broth allows manipulation of mass transfer independently of gas flow.

In particular embodiments, the fresh gas is introduced into the vessel by one or more gas inlets. Typically, high mass transfer rates can be achieved by introducing the gaseous substrate as fine bubbles. Those skilled in the art will appreciate means for introducing gaseous substrate, such as spargers. In particular embodiments, the gas is introduced into the vessel by fine bubble diffusers.

Upon consideration of the instant disclosure, those skilled in the art will appreciate the size and type of pump required to circulate fermentation broth comprising one or more micro-organisms around the closed loop. It must be noted that the higher the gas hold up in the liquid, the less dense the liquid, so the pump needs to be configured to circulate liquids of varying densities as the composition of the gas/liquid slurry changes. By way of non limiting example, one or more multiphase pumps configured for pumping the fermentation broth/gas slurry can be used to circulate the slurry. Centrifugal pumps are typically used to circulate single phase liquids and increase the discharge pressure of a fluid. Using a rotating impeller, liquid enters the pump along the rotating shaft of the motor and accelerates the liquid radially outward through a diffuser chamber. Centrifugal pumps can also operate with lower two phase gas hold ups without cavitating (a known vulnerability of centrifugal pumps), by maintaining an adequate net positive suction head. Those skilled in the art will appreciate there are multiphase pumping solutions available for large scale applications.

Upon consideration of the instant disclosure, those skilled in the art will appreciate there are a wide range of suitable gas/liquid contact modules that can provide effective mass transfer of a gaseous substrate necessary to improve the efficiency of microbial fermentations. A contact module provides a unique geometrical environment allowing gas and liquid to mix thoroughly along a set flow path, causing the entrained gas to dissolve in the liquid more uniformly. At a fixed gas volume, this increases the surface area of the gaseous substrate available for the microbes to convert into metabolites thus increasing the efficiency of the fermentation process. By way of example, these contact modules include, but are not limited to a matrix of structured corrugated metal packing, random packing, sieve plates and static mixers, all of which have a range of well-known types and densities and are widely commercially available.

There are a number of known contact modules that can provide high mass transfer rates required for efficient fermentation. However, this is usually at the expense of a high pressure differential across the module resulting in a low efficiency. The pressure differential being the difference in pressure between either ends of the contact module. It requires a higher net energy input to overcome a higher pressure drop via a mechanical circulation pump.

Structured corrugated metal packing inherently creates a longer flow path for the liquid/gas medium to follow due to the series of flow restrictions the medium must overcome inside the packing causing a longer resonance time. At higher flows, the packing causes high turbulence and mixing therefore higher mass transfer rates, at the expense of a higher pressure differential attributable to a more restricted flow path. Jaegar Metal MAX-PAK and Raschig Super Pak structured packing surface area to volume ratios tested include 100, 250, 500, & 750 $m^2/m^3$.

Static mixers have a shorter flow path than structured packing on average. Static mixers have shown more effective mass transfer rates however the efficiencies based on the pressure drop across the modules is still being tested. Newer static mixer designs such as the Sulzer SMX plus has been optimized with computational fluid dynamics to maintain the same high mass transfer rates at a 50% less pressure drop of the original SMX design. Sulzer SMX plus static mixer from 200 mm diameter up to 500 mm diameter provides excellent mixing of a wide range of liquids and gases at various viscosities at a lower shear stress than structured packing.

According to particular aspects of the invention, there is provided a novel gas/liquid contact module for fermentation of one or more gaseous substrates, the contact module comprising multiple channels. In particular embodiments of the invention, the contact module provides effective mass transfer of a gaseous substrate, such as a gaseous substrate comprising CO and optionally H2, to one or more micro-organisms in a liquid media. According to certain embodiments, the substrate is provided to one or more carboxydotrophic microorganisms such that products including one or more acid(s) and/or alcohol(s) are produced.

Suitable gas/liquid contact modules are well known in the art and are typically employed for increasing efficiency of mass transfer in a gas/liquid catalytic reaction, or a gas/solid catalytic reaction. Typical modules are exemplified and discussed in Kreutzer et al. *Catalysis Today;* 2006, 111, pp 111-118, which is fully incorporated herein by reference. Such modules comprise multiple, typically straight, parallel channels. The channels are configured such that liquid and gas can pass through. As a gas bubble passes through the channel, it pushes through the liquid transiently forming a thin film of liquid between the bubble and the wall of the channel. This allows components of the gas bubble, for example substrate(s) such as CO and/or H2 to efficiently pass into the thin film of liquid, thus increasing mass transfer across the gas/liquid interface. The movement of the gas bubble through the liquid in the channel approximates Taylor flow. As the pressure drop across the module is relatively small, high mass transfer rates can be achieved with lower power inputs compared to other well known gas/liquid contact reactors, such as trickle bed reactors, slurry bed reactors, bubble columns and airlift reactors.

It has been surprisingly recognised that such contact modules can be used to increase mass transfer of a substrate to micro-organisms in a liquid media. Thus, according to particular embodiments of the invention, there is provided a method of improving efficiency of fermentation of a gaseous substrate, particularly a substrate comprising CO and optionally H2, by one or more microorganisms in a liquid medium. By improving mass transfer of the substrate, it is considered that elevated growth and/or metabolite production rates can be achieved and/or overall power usage reductions compared to conventional known bioreactors, such as CSTR, bubble columns, gas lift fermenters.

The gas/liquid contact modules suitable for use in embodiments of the invention comprise multiple, typically straight, parallel channels in a solid matrix. Typical matrices include a substantially solid block known as a monolith, wherein channels are separated by walls of a ceramic material. Ceramic materials typically used in monoliths include cordierite, porcelain, mullite, alumina and stoneware, which can be extruded to form the module comprising multiple channels.

Alternatively, the module can be constructed from extruded plastic material or multiple corrugated layers of a resiliently flexible material such as metal or plastic, laid such that multiple channels run through the length of the module.

The channels running though the module are typically straight and parallel to provide minimal resistance to liquid and gas passing through. However, in particular embodiments, the channels can include curved portions, such that a continuous or broken loop can be formed. In particular embodiments, the channels are typically configured such that Taylor flow of the liquid/gas components is promoted. For example, the diameter of the channel's can range from approximately 0.5 mm to at least 5 mm. However, in particular embodiments the channels have a diameter of approx 2-5 mm. Furthermore, the channels can range from several centimeters to 10's of meters in length.

The geometry or internal characteristics of the channels can also be configured to assist in optimising mass transfer within the channel, for example by optimising turbulence and/or stabilising the gas/liquid interface. For example, indentations and/or protrusions such as fins can improve flow dynamics and/or mass transfer in the channels. Various channel geometries are exemplified in Kreutzer et al. *Catalysis Today* (ibid). For example, the channels can be punched with holes to allow channel to channel movement of fluids or corrugated transverse to the flow direction.

Geometry and size of the channels will also determine how the module is optimally operated. For example, the gas and liquid can be introduced into the module co-currently (both flowing in the same direction) or counter-currently. Accordingly, liquid can be introduced from the top and allowed to flow down through the module while gas can be introduced from the bottom or top. In alternative embodiments, wherein gas is introduced at the bottom of a module, the bubbles buoyancy can assist in maintaining a liquid/gas flow from the bottom to the top of a module. In other embodiments, the liquid and/or gas are driven through the module by mechanical means, such as pump(s) and/or compressor(s). In such embodiments, the direction of flow is unimportant and can be up, down, sideways or a combination thereof. In particular embodiments, a bioreactor containing the module is part of a loop, wherein liquid exiting the module is returned to the module, such that a substantially continuous flow is maintained. Gas can be optionally separated from the liquid using any known separation means and returned to the bioreactor or exhausted.

In accordance with the invention, the novel contact module is included in a bioreactor configured to receive a gaseous substrate such that fermentation of the substrate by one or more microorganisms can occur. The bioreactor will typically comprise a vessel to enclose the microbial culture, which is typically, at least in part, suspended in aqueous fermentation broth. The bioreactor will also typically include means for introducing and removing gas streams and liquid streams and configured for monitoring and controlling a variety of parameters such as pH, ORP and temperature.

One or more contact modules can be used with gas driven, liquid driven or gas/liquid driven bioreactors. Upon consideration of the instant disclosure, those skilled in the art will appreciate suitable bioreactor configurations. However, by way of non-limiting example, suitable gas driven bioreactors include bubble columns, internal or external loop gas-lift bioreactors and deep-shaft fermenters. For example, one or more contact modules can be provided in the riser and/or down-corner of a gas-lift bioreactor to improve mass transfer of the substrate.

Additionally or alternatively, when a microbial culture is not easily damaged by fluid shear, liquid driven bioreactors, such as circulated liquid loop bioreactors, jet loop bioreactors or propeller loop bioreactors can be used with one or more contact modules of the invention. Various configurations of forced circulation loop reactors with externally located pumps have been previously described and can be used in accordance with the invention. By way of example, several such bioreactors are detailed in Fadavi et al. "Gas-Liquid mass transfer in a novel forced circulation loop reactor" *Chemical Engineering Journal*, 112 (2005), 73-80, which is fully incorporated herein by reference. Typically, a pump, such as a centrifugal pump, is used to force a jet of liquid (fermentation broth) either upwards or downwards in a draft tube that is typically concentrically or adjacently located in an outer vessel. In accordance with particular embodiments of the invention, one or more modules can be included in the riser and/or down-corner of a circulated loop reactor to improve mass transfer of the substrate.

The bioreactor may also include means for evenly distributing a gas stream prior to introduction into the contact module. For example, a bioreactor may include one or more static mixers, perforated plates and/or baffles upstream of the contact module, configured to substantially homogenise a gaseous stream to optimise mass transfer in the channels of the module.

The rate at which fluid passes through the gas/liquid contact module will be partially dependent on the total cross-sectional area of all of the channels. As such, the channel density also needs to be considered when determining how the module is optimally operated. The channel density will depend on the channel size and the channel wall thickness which may be a function of the construction material. For example, an extruded ceramic material may include 1-10's of channels per square inch (cpsi), whereas a module constructed of rolled corrugated foil or plastic material may include hundreds of channels per square inch. By way of non-limiting example, a square channelled ceramic contact module with 5 mm diameter channels typically comprises approx 15-25 cpsi, whereas 2 mm channels typically comprise approx 150-200 cpsi.

It is recognised that the size and geometry of the channel(s) will have an influence on the flow characteristics of the gas/liquid through the module. For example, typically, Taylor flow can be achieved in channels of approx 1 mm-5 mm. However, larger diameter channels typically promote a falling film effect as liquid trickles down the inner walls of the channels. High mass transfer rates can be achieved in accordance with the methods of the invention, in the Taylor flow and falling film embodiments.

The microorganisms can be simply carried through the module suspended in the liquid phase, which will typically be an aqueous solution of nutrients required for microbial growth and metabolite production. Additionally or alternatively, the micro-organism(s) can form a biofilm on the internal surfaces of the channels and the liquid phase substantially continuously in contact with the biofilm supplying essential nutrients. The substrate is efficiently provided to the microorganism(s) as the gas comprising the substrate passes through the channels. In particular embodiments of the invention, the module or parts of the module, particularly the channel components of the module, is constructed of material suitable for attachment of a microbial biofilm. Suitable materials include porous or semi porous materials, such as ceramic materials, plastic materials, such as polypropylene or polyethylene.

DEFINITIONS

Unless otherwise defined, the following terms as used throughout this specification are defined as follows:

"Gaseous substrate" includes any gas which contains a compound or element used by a microorganism as a carbon source and optionally energy source in fermentation.

"Gaseous substrates comprising carbon monoxide" include any gas which contains carbon monoxide. The gaseous substrate will typically contain a significant proportion of CO, preferably at least about 5% to about 95% CO by volume.

The term "bioreactor" includes devices and vessels for gas/liquid contact, suitable for conducting a desired fermentation.

The term "mass transfer" as used herein relates to the transfer of atoms or molecules, particularly substrate atoms or molecules from a gaseous phase into an aqueous solution.

The term "biofilm" relates to an aggregation of one or more microorganism(s) adhered to a surface.

The term "acid" as used herein includes both carboxylic acids and the associated carboxylate anion, such as the mixture of free acetic acid and acetate present in a fermentation broth as described herein. The ratio of molecular acid to carboxylate in the fermentation broth is dependent upon the pH of the system. In addition, the term "acetate" includes both acetate salt alone and a mixture of molecular or free acetic acid and acetate salt, such as the mixture of acetate salt and free acetic acid present in a fermentation broth as described herein.

Unless the context requires otherwise, the phrases "fermenting", "fermentation process" or "fermentation reaction" and the like, as used herein, are intended to encompass both the growth phase and product biosynthesis phase of the process.

The terms "increasing the efficiency", "increased efficiency" and the like, when used in relation to a fermentation process, include, but are not limited to, increasing one or more of: the rate of growth of micro-organisms in the fermentation, the volume or mass of desired product (such as alcohols) produced per volume or mass of substrate (such as carbon monoxide) consumed, the rate of production or level of production of the desired product, and the relative proportion of the desired product produced compared with other by-products of the fermentation, and further may reflect the value (which may be positive or negative) of any by-products generated during the process.

While certain embodiments of the invention, namely those that include the production of ethanol by anaerobic fermentation using CO and optionally H2 as the primary substrate, are readily recognized as being valuable improvements to technology of great interest today, it should be appreciated that the invention is applicable to production of alternative products such as other alcohols and the use of alternative substrates, particularly gaseous substrates, as will be known by persons of ordinary skill in the art to which the invention relates upon consideration of the instant disclosure. For example, gaseous substrates containing carbon dioxide and hydrogen may be used in particular embodiments of the invention. Similar gaseous substrates such as CH4 and/or H2S may also be used in particular embodiments. Further, the invention may be applicable to fermentations to produce alternative products, such as acetate, butyrate, propionate, caproate, ethanol, propanol, and butanol, and hydrogen. By way of example, these products may be produced by fermentation using microbes from the genus *Moorella*, *Clostridia*, *Ruminococcus*, *Acetobacterium*, *Eubacterium*, *Butyribacterium*, *Oxobacter*, *Methanosarcina*, *Methanosarcina*, and *Desulfotomaculum*.

Fermentation Reaction

Particular embodiments of the invention include the fermentation of a CO containing substrate and/or syngas substrate stream to produce products including alcohol(s) and optionally acid(s). Processes for the production of ethanol and other alcohols from gaseous substrates are known. Exemplary processes include those described for example in WO2007/117157, WO2008/115080, U.S. Pat. No. 6,340,581, U.S. Pat. No. 6,136,577, U.S. Pat. No. 5,593,886, U.S. Pat. No. 5,807,722 and U.S. Pat. No. 5,821,111, each of which is incorporated herein by reference.

A number of anaerobic bacteria are known to be capable of carrying out the fermentation of CO to alcohols, including n-butanol and ethanol, and acetic acid, and are suitable for use in the process of the present invention. Examples of such bacteria that are suitable for use in the invention include those of the genus *Clostridium*, such as strains of *Clostridium ljungdahlii*, including those described in WO 00/68407, EP 117309, U.S. Pat. Nos. 5,173,429, 5,593,886, and 6,368,819, WO 98/00558 and WO 02/08438, *Clostridium carboxydivorans* (Liou et al., International Journal of Systematic and Evolutionary Microbiology 33: pp 2085-2091), *Clostridium ragsdalei* (WO/2008/028055) and *Clostridium autoethanogenum* (Abrini et al, Archives of Microbiology 161: pp 345-351). Other suitable bacteria include those of the genus *Moorella*, including *Moorella* sp HUC22-1, (Sakai et al, Biotechnology Letters 29: pp 1607-1612), and those of the genus *Carboxydothermus* (Svetlichny, V. A., Sokolova, T. G. et al (1991), Systematic and Applied Microbiology 14: 254-260). Further examples include *Morella thermoacetica*, *Moorella thermoautotrophica*, *Ruminococcus productus*, *Acetobacterium woodii*, *Eubacterium limosum*, *Butyribacterium methylotrophicum*, *Oxobacter pfennigii*, *Methanosarcina barkeri*, *Methanosarcina acetivorans*, *Desulfotomaculum kuznetsovii* (Simpa et. al. Critical Reviews in Biotechnology, 2006 Vol. 26. Pp 41-65). In addition, it should be understood that other carboxydotrophic anaerobic bacteria may be applicable to the present invention as would be understood by a person of skill in the art. It will also be appreciated that the invention may be applied to a mixed culture of two or more bacteria.

One exemplary micro-organism suitable for use in the present invention is *Clostridium autoethanogenum*. In one embodiment, the *Clostridium autoethanogenum* is a *Clostridium autoethanogenum* having the identifying characteristics of the strain deposited at the German Resource Centre for Biological Material (DSMZ) under the identifying deposit number 19630. In another embodiment, the *Clostridium autoethanogenum* is a *Clostridium autoethanogenum* having the identifying characteristics of DSMZ deposit number DSMZ 10061.

Culturing of the bacteria used in the methods of the invention may be conducted using any number of processes known in the art for culturing and fermenting substrates using anaerobic bacteria. Exemplary techniques are provided in the "Examples" section below. By way of further example, those processes generally described in the following articles using gaseous substrates for fermentation may be utilised: (i) K. T. Klasson, et al. (1991). Bioreactors for synthesis gas fermentations resources. Conservation and Recycling, 5; 145-165; (ii) K. T. Klasson, et al. (1991). Bioreactor design for synthesis gas fermentations. Fuel. 70. 605-614; (iii) K. T. Klasson, et al. (1992). Bioconversion of synthesis gas into liquid or gaseous fuels. Enzyme and Microbial Technology. 14; 602-608; (iv) J. L. Vega, et al. (1989). Study of Gaseous Substrate Fermentation Carbon Monoxide Conversion to Acetate. 2. Continuous Culture. Biotech. Bioeng. 34. 6. 785-793; (vi) J. L. Vega, et al. (1989). Study of gaseous substrate fermentations: Carbon monoxide conversion to acetate. 1. Batch culture. Biotechnology and Bioengineering. 34. 6. 774-784; (vii) J. L. Vega, et al. (1990). Design of Bioreactors for Coal Synthesis Gas Fermentations. Resources, Conservation and Recycling. 3. 149-160; all of which are incorporated herein by reference.

The fermentation is carried out in a bioreactor comprising one or more gas/liquid contact modules comprising multiple channels. Microorganisms can be inoculated into the bioreactor and a gaseous substrate provided, wherein microbial growth and metabolite production can occur. Additionally, or alternatively, the microorganism(s) can be cultured in a separate growth reactor and then substantially continuously provided to the bioreactor containing the module, wherein further growth, biofilm formation and/or metabolite production can occur.

According to various embodiments of the invention, the carbon source for the fermentation reaction is a gaseous substrate containing CO. The substrate may be a CO-containing waste gas obtained as a by-product of an industrial process, or from some other source such as from automobile exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing substrate may be captured from the industrial process before it is emitted into the atmosphere, using any convenient method. Depending on the composition of the CO-containing substrate, it may also be desirable to treat it to remove any undesired impurities, such as dust particles before introducing it to the fermentation. For example, the gaseous substrate may be filtered or scrubbed using known methods.

Alternatively, the CO-containing substrate may be syngas sourced from the gasification of biomass. The process of gasification involves partial combustion of biomass in a restricted supply of air or oxygen. The resultant gas typically comprises mainly CO and $H_2$, with minimal volumes of $CO_2$, methane, ethylene and ethane. For example, biomass by-products obtained during the extraction and processing of foodstuffs such as sugar from sugarcane, or starch from maize or grains, or non-food biomass waste generated by the forestry industry may be gasified to produce a CO-containing syngas suitable for use in the present invention.

The CO-containing substrate will typically contain a major proportion of CO, such as at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

It is recognised that mass transfer rate of CO into an aqueous media is proportional to the partial pressure of a gaseous substrate comprising CO. As such, the mass transfer rate can be increased by increasing the proportion of CO in a gas stream by enrichment or removal of unwanted components, such as inert components. Additionally, partial pressure of CO can be increasing the pressure of a gaseous substrate stream.

While it is not necessary for the substrate to contain any hydrogen, the presence of $H_2$ should not be detrimental to product formation in accordance with methods of the invention. In particular embodiments, the presence of hydrogen results in an improved overall efficiency of alcohol production. For example, in particular embodiments, the substrate may comprise an approx 2:1, or 1:1, or 1:2 ratio of H2:CO. In other embodiments, the substrate stream comprises low concentrations of H2, for example, less than 5%, or less than 4%, or less than 3%, or less than 2%, or less than 1%, or is substantially hydrogen free. The substrate may also contain some $CO_2$ for example, such as about 1% to about 80% $CO_2$ by volume, or 1% to about 30% $CO_2$ by volume.

It will be appreciated that for growth of the bacteria and CO-to-alcohol fermentation to occur, in addition to the CO-containing substrate gas, a suitable liquid nutrient medium will need to be fed to the bioreactor. A nutrient medium will contain vitamins and minerals sufficient to permit growth of the micro-organism used. Anaerobic media suitable for the fermentation of ethanol using CO as the sole carbon source are known in the art. For example, suitable media are described in U.S. Pat. Nos. 5,173,429 and 5,593,886 and WO 02/08438, WO2007/117157, WO2008/115080 and WO2009/022925, referred to above. The present invention provides a novel media which has increased efficacy in supporting growth of the micro-organisms and/or alcohol production in the fermentation process. This media will be described in more detail hereinafter.

The fermentation should desirably be carried out under appropriate conditions for the desired fermentation to occur (e.g. CO-to-ethanol). Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition. Suitable conditions are described in WO02/08438, WO2007/117157, WO2008/115080 and WO2009/022925. The optimum reaction conditions will depend partly on the particular microorganism used. However, in general, it is preferred that the fermentation be performed at pressure higher than ambient pressure. Operating at increased pressures allows a significant increase in the rate of CO transfer from the gas phase to the liquid phase where it can be taken up by the microorganism as a carbon source for the production of ethanol. This in turn means that the retention time (defined as the liquid volume in the bioreactor divided by the input gas flow rate) can be reduced when bioreactors are maintained at elevated pressure rather than atmospheric pressure.

Furthermore, the rate at which substrate comprising CO is made available to the microorganisms also affects the rate or efficiency of growth and product formation. For example, fermentation conditions wherein a substrate is limited typically lead to slower metabolism and the production of unwanted by-products. Conversely, excess substrate can lead to inhibition of the metabolism of the microorganisms, a cessation of growth and potentially cell death. PCT/NZ2010/000009, which is fully incorporated herein by reference, details methods of supply a gaseous substrate comprising CO to a microbial culture at or towards an optimum rate.

The benefits of conducting a gas-to-ethanol fermentation at elevated pressures have also been described elsewhere. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per liter per day.

It is also desirable that the rate of introduction of the CO-containing gaseous substrate is such as to ensure that the concentration of CO in the liquid phase does not become limiting. This is because a consequence of CO-limited conditions may be that the ethanol product is consumed by the culture.

Product Recovery

The products of the fermentation reaction can be recovered using known methods. Exemplary methods include those described in WO2007/117157, WO2008/115080, WO2009/022925, U.S. Pat. No. 6,340,581, U.S. Pat. No. 6,136,577, U.S. Pat. No. 5,593,886, U.S. Pat. No. 5,807,722 and U.S. Pat. No. 5,821,111. However, briefly and by way of example only ethanol may be recovered from the fermentation broth by methods such as fractional distillation or evaporation, and extractive fermentation.

Distillation of ethanol from a fermentation broth yields an azeotropic mixture of ethanol and water (i.e., 95% ethanol and 5% water). Anhydrous ethanol can subsequently be obtained through the use of molecular sieve ethanol dehydration technology, which is also well known in the art.

Extractive fermentation procedures involve the use of a water-miscible solvent that presents a low toxicity risk to the fermentation organism, to recover the ethanol from the dilute fermentation broth. For example, oleyl alcohol is a solvent that may be used in this type of extraction process. Oleyl alcohol is continuously introduced into a fermenter, whereupon this solvent rises forming a layer at the top of the fermenter which is continuously extracted and fed through a centrifuge. Water and cells are then readily separated from the oleyl alcohol and returned to the fermenter while the ethanol-laden solvent is fed into a flash vaporization unit. Most of the ethanol is vaporized and condensed while the oleyl alcohol is non volatile and is recovered for re-use in the fermentation.

Acetate, which is produced as by-product in the fermentation reaction, may also be recovered from the fermentation broth using methods known in the art.

For example, an adsorption system involving an activated charcoal filter may be used. In this case, it is preferred that microbial cells are first removed from the fermentation broth using a suitable separation unit. Numerous filtration-based methods of generating a cell free fermentation broth for product recovery are known in the art. The cell free ethanol—and acetate—containing permeate is then passed through a column containing activated charcoal to adsorb the acetate. Acetate in the acid form (acetic acid) rather than the salt (acetate) form is more readily adsorbed by activated charcoal. It is therefore preferred that the pH of the fermentation broth is reduced to less than about 3 before it is passed through the activated charcoal column, to convert the majority of the acetate to the acetic acid form.

Acetic acid adsorbed to the activated charcoal may be recovered by elution using methods known in the art. For example, ethanol may be used to elute the bound acetate. In certain embodiments, ethanol produced by the fermentation process itself may be used to elute the acetate. Because the boiling point of ethanol is 78.8° C. and that of acetic acid is 107° C., ethanol and acetate can readily be separated from each other using a volatility-based method such as distillation.

Other methods for recovering acetate from a fermentation broth are also known in the art and may be used in the processes of the present invention. For example, U.S. Pat. Nos. 6,368,819 and 6,753,170 describe a solvent and cosolvent system that can be used for extraction of acetic acid from fermentation broths. As with the example of the oleyl alcohol-based system described for the extractive fermentation of ethanol, the systems described in U.S. Pat. Nos. 6,368,819 and 6,753,170 describe a water immiscible solvent/co-solvent that can be mixed with the fermentation broth in either the presence or absence of the fermented micro-organisms in order to extract the acetic acid product. The solvent/co-solvent containing the acetic acid product is then separated from the broth by distillation. A second distillation step may then be used to purify the acetic acid from the solvent/co-solvent system.

The products of the fermentation reaction (for example ethanol and acetate) may be recovered from the fermentation broth by continuously removing a portion of the broth from the fermentation bioreactor, separating microbial cells from the broth (conveniently by filtration), and recovering one or more product from the broth simultaneously or sequentially. In the case of ethanol it may be conveniently recovered by distillation, and acetate may be recovered by adsorption on activated charcoal, using the methods described above. The separated microbial cells are preferably returned to the fermentation bioreactor. The cell free permeate remaining after the ethanol and acetate have been removed is also preferably returned to the fermentation bioreactor. Additional nutrients (such as B vitamins) may be added to the cell free permeate to replenish the nutrient medium before it is returned to the bioreactor. Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

Novel Gas/Liquid Contact Module and Bioreactor

Figure 1:
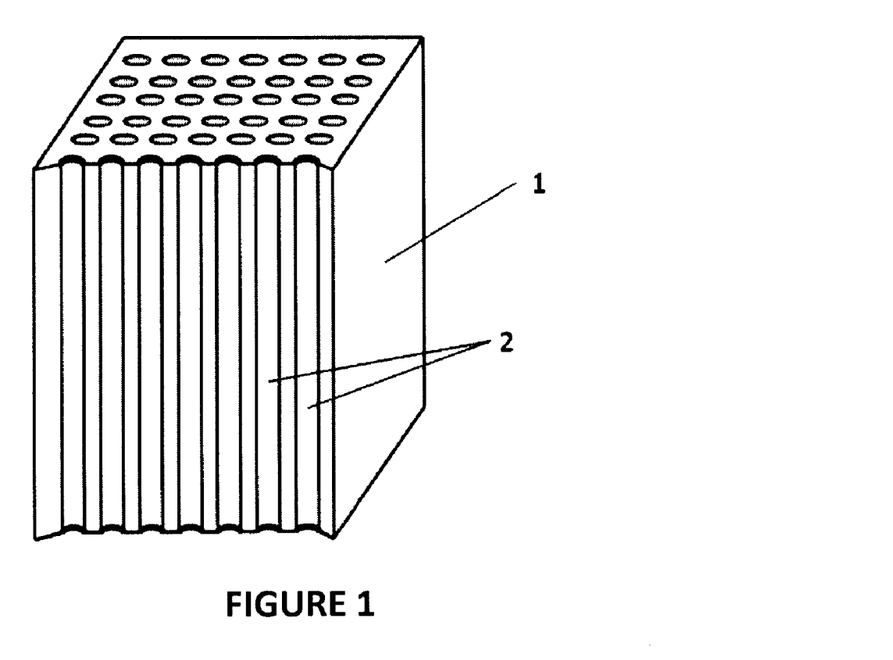
FIG. 1 is a schematic cutaway representation of a gas/liquid contact module comprising multiple channels.

FIG. 1 is a schematic cutaway representation of a contact module 1 comprising multiple channels 2. In accordance with the invention, a bioreactor comprising one or more modules is configured such that in use, gas and liquid flow through the channels. The liquid phase is typically a liquid media comprising nutrients required to support microbial growth and metabolite production. The liquid can flow through the module in either direction and may be pumped through the channels, flow through the channels under gravity and/or be pushed through the channels by the moving gas phase, or a combination thereof.

The substrate gas can be passed through the channels in either direction, either driven by their own buoyancy or pumped through (or a combination thereof). As the bubbles travel through the narrow channels, efficient mass transfer is achieved. The channels are configured to optimise gas/liquid contact by promoting Taylor flow or a falling film effect, wherein improved mass transfer occurs between the substrate gas and a thin film of liquid formed against the channel wall. The mechanism of operation will depend largely on the size and/or geometry of the channels. For example, optimal Taylor flow of water may be achieved with channels of approx 1-5 mm diameter, whereas a wider diameter will be suitable for the falling film.

Figure 2:
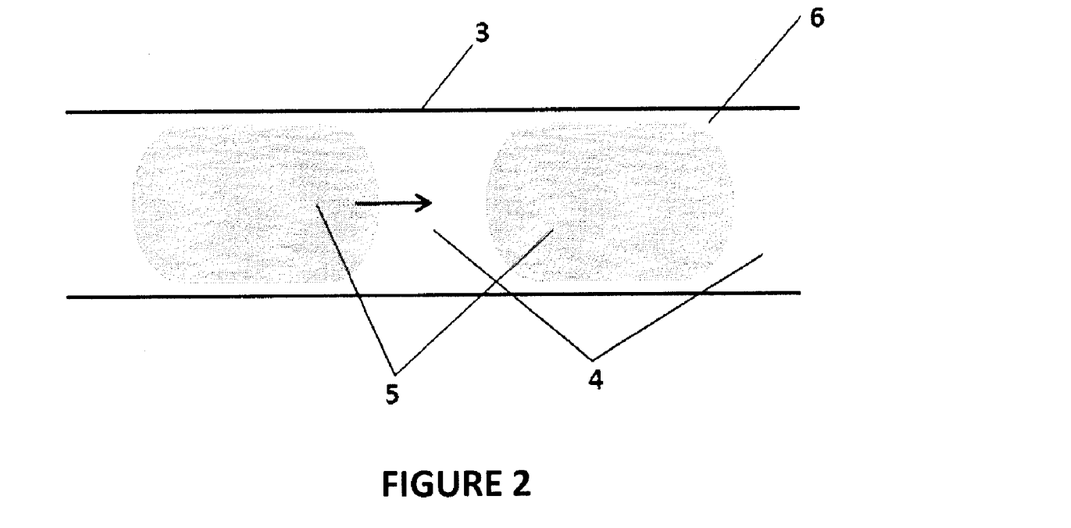
FIG. 2 is a diagrammatic representation of Taylor flow through a channel.

FIG. 2 is a diagrammatic representation of Taylor flow through a channel 3. Slugs of liquid 4 are pushed through the channel 3 at a rate. However, the gas bubbles 5 move through the channel at a slightly faster rate, such that they push through the slower moving liquid thus forming a thin liquid film 6 against the side of the channel 3 as they pass. As the bubble 5 propagates along the channel 3, the thin film 6 also moves along the channel 3 at the same rate. Increased mass transfer occurs at the interface of the gas bubble 5 and the thin liquid film 6.

Figure 3A:
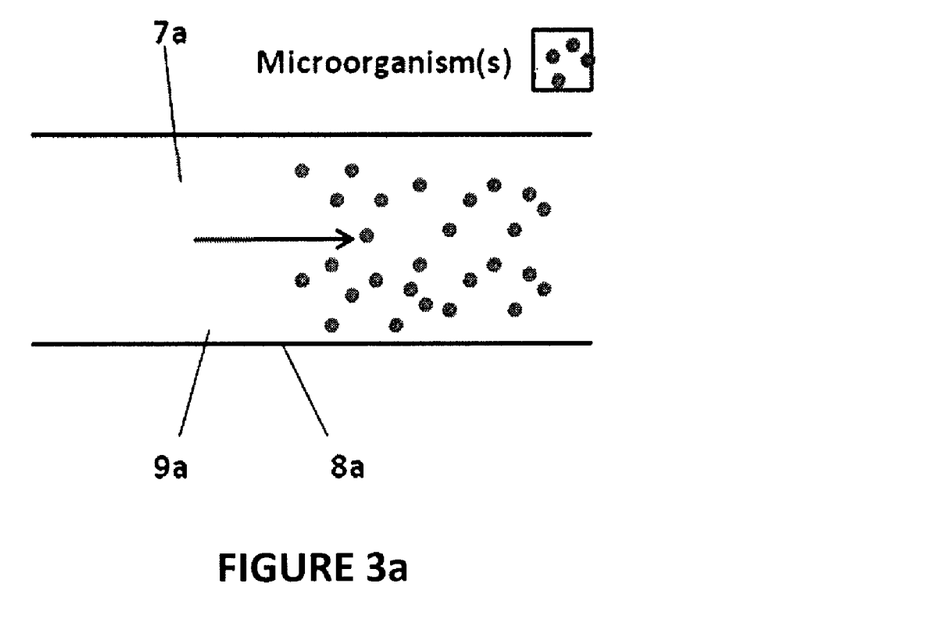
FIG. 3*a* shows a schematic representation of microorganism(s) suspended in liquid media.

FIG. 3a shows a schematic representation of microorganism suspended in liquid media. As the gas bubble 7a propagates along the channel 8a, the thin film region 9a, of high mass transfer also propagates, such that the substrate is provided at elevated rates to microorganisms in the region of the thin film 9a.

Figure 3B:
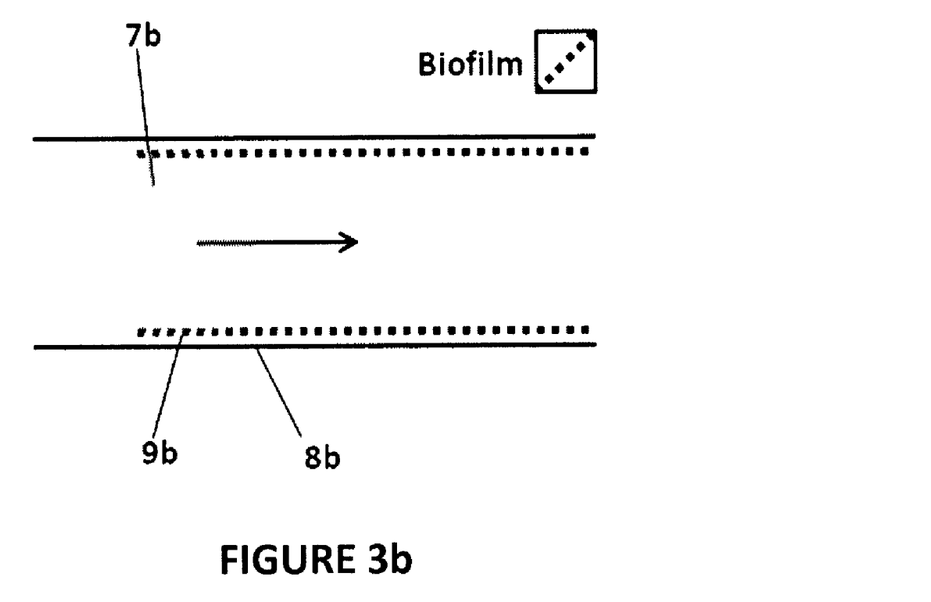
FIG. 3*b* shows a schematic representation of a biofilm of microorganism(s) formed against the inner walls of a channel.

FIG. 3b shows a schematic representation of a biofilm of microorganism formed against the inner walls of the channel. As the gas bubble 7b propagates along the channel 8b, the substrate is provided to the biofilm at elevated rates in the region of the thin liquid film 9b.

Figure 4:
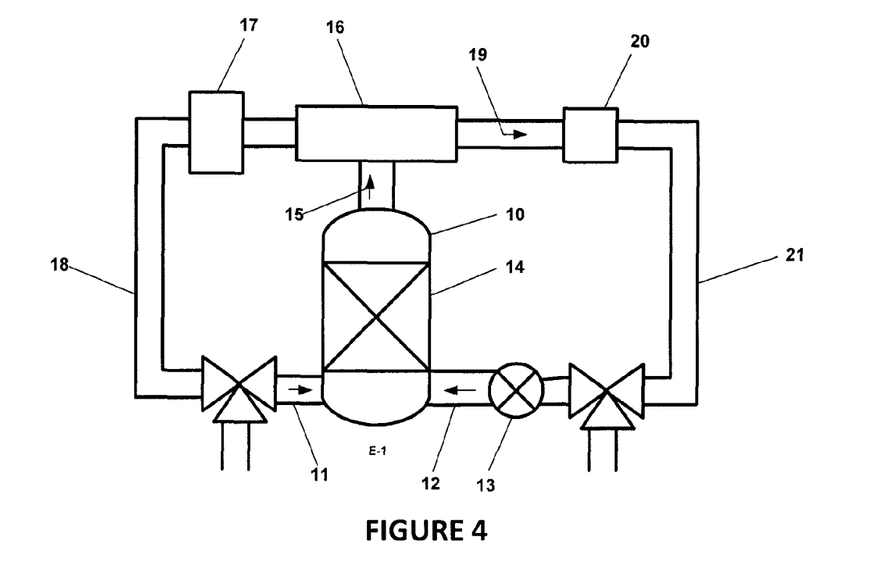
FIG. 4 is a schematic diagram of a system including a bioreactor of the instant invention.

FIG. 4 is a schematic diagram of a system including a bioreactor of the instant invention. In operation, microorganisms are cultivated in bioreactor 10. Liquid media can be introduced into bioreactor 10 via inlet 11. The liquid can be pumped through bioreactor 10 to maintain a substantially continuous flow, or the flow can be driven by the gas entering the bioreactor 10 by inlet 12. A gas stream can be optionally compressed prior to introduction by compressor 13. The gas and liquid are introduced into bioreactor 10, wherein they pass through gas/liquid contact portion 14. In particular embodiments, the gas/liquid contact portion is the contact module described herein. It is recognised that the products produced by the microorganism will be carried away from the bioreactor 10 in combined gas/liquid exit stream 15. The liquid and gas phases can be separated by any known separation means 16. It is recognised that at least a portion of the product will be dissolved in the separated liquid stream. The products can be recovered by any known recovery means 17. The liquid can then be optionally returned to the bioreactor 10, via conduit 18. Similarly, products can optionally be removed from gaseous stream 19 by any known product recovery means 20 and said stream optionally returned to bioreactor 10, via conduit 21.

Figure 5:
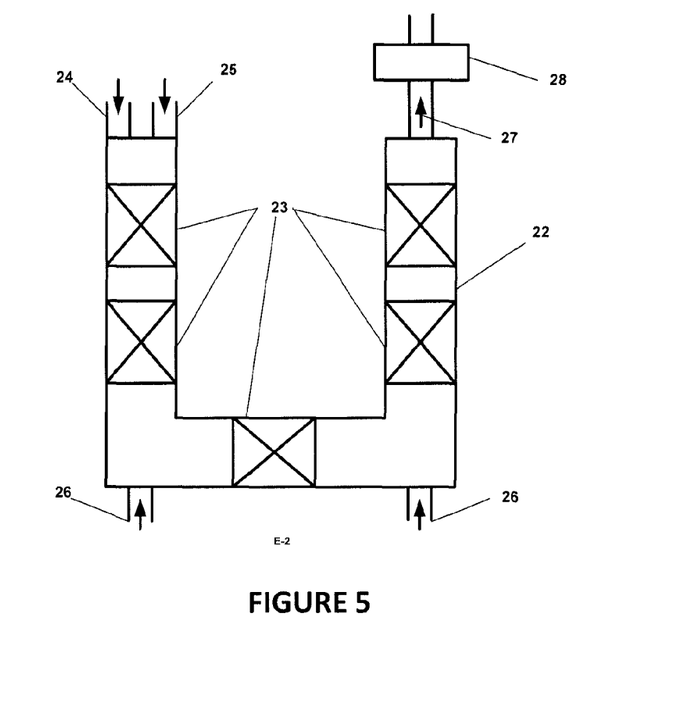
FIG. 5 is a schematic representation of one embodiment of the invention.

FIG. 5 is a schematic representation of one embodiment of the invention, wherein bioreactor 22 comprises multiple packing portions 23, such as the novel contact module, arranged in a loop configuration. Substrate containing gas and liquid can enter the bioreactor through inlets 24 and 25 respectively. Optionally gas inlets 26 can be included at further points along the length of the loop bioreactor 22, to replenish gas streams where the substrate has been depleted. In operation, the gas/liquid flows through the modules 23 and at least a portion of the substrate is converted to products. The products will be carried out of the bioreactor 22 in gas/liquid exit stream 27. A gas/liquid separator 28 separates the gas and liquid components of the exit stream 27, wherein products can be optionally removed from the gas and/or liquid components. Furthermore, the gas and/or liquid components can be optionally returned to the bioreactor inlet 24 and/or 25 and recycled through the system.

Figure 6:
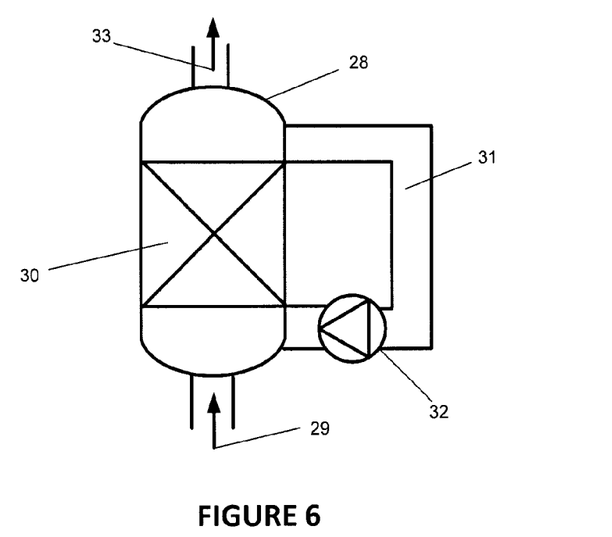
FIG. 6 is a schematic representation of one embodiment of the invention.

FIG. 6 is a schematic diagram of a circulated liquid loop bioreactor. In operation, microorganisms are cultured in a liquid fermentation broth in bioreactor 28 and gaseous substrate can be introduced via inlet port 29. The gaseous substrate can be sparged into the bioreactor by any known sparging means. However, in particular embodiments, the gas is introduced through one or more fine bubble spargers or diffusers. The bioreactor 28 includes a gas/liquid contact portion 30, which in particular embodiments comprises one or more contact modules. In another embodiment, the contact portion includes alternative means for promoting gas/liquid contact, such as static mixers, baffles and/or perforated plates. In particular embodiments, portion 30 can be switched out with alternative packing portions such that mass transfer performance can be compared. The fermentation broth is circulated around the down-corner portion of the loop 31, by means of a pump 32. The pump may be any suitable liquid transfer device known in the art, however, in particular embodiments; the pump is a centrifugal pump. Unconverted gaseous substrate and/or gaseous waste can exit bioreactor 28 via outlet port 33.

In particular embodiments of the invention, the bioreactor includes at least one gas/liquid contact module fabricated of rolled corrugated stainless steel foil of approx 45 mm diameter and approximately 960 mm in length. In such embodiments, the longitudinally aligned corrugations layered over each other provide multiple channels for gas/liquid contact, running through the module. The channel density is approximately 600 channels per square inch and the channel has a cross sectional diameter of approx 1.17 mm. In another embodiment, the channel density is approx 400 channels per square inch and each channel has a cross-sectional diameter of approx 1.43 mm. In particular embodiments, the gas/liquid contact module includes a transverse corrugation rolled into the foil to provide a protrusion into the flow channel that induces perturbation into the fluid flowing in the channel.

In particular embodiments, the bioreactor includes one or more mixing means upstream of the gas/liquid contact module to evenly distribute the gas and liquid prior to entry into the module. Mixing means are well known in the art and include internal mixers, such as static mixers, baffles or perforated plates. In particular embodiments, the bioreactor includes one or more static mixers, such as a six element semi ellipsoidal static mixer upstream of each module such that the gas and liquid entering the module is substantially uniformly distributed across the channels.

EXAMPLES

Materials and Methods

| Solution A | | | |
|---|---|---|---|
| $NH_4Ac$ | 3.083 g | KCl | 0.15 g |
| $MgCl_2 \cdot 6H_2O$ | 0.61 g | | |
| $CaCl_2 \cdot 2H_2O$ | 0.294 g | Distilled Water | Up to 1 L |
| Solution B | | | |
| Biotin | 20.0 mg | Calcium D-(*)- pantothenate | 50.0 mg |
| Folic acid | 20.0 mg | | |
| Pyridoxine•HCl | 10.0 mg | Vitamin B12 | 50.0 mg |
| Thiamine•HCl | 50.0 mg | p-Aminobenzoic acid | 50.0 mg |
| Riboflavin | 50.0 mg | Thioctic acid | 50.0 mg |
| Nicotinic acid | 50.0 mg | Distilled water | To 1 Liter |
| 0.1 mol/L stock metal solutions (C) | | | |
| $FeCl_2 \cdot 4H_2O$ solution 0.1M | 80 mL | $H_3BO_3$ solution 0.1M | 8 mL |
| $CoCl_2 \cdot 6H_2O$ solution 0.1M | 40 mL | $NaMoO_4 \cdot 2H_2O$ solution 0.1M | 8 mL |
| $NiCl_2 \cdot 6H_2O$ solution 0.1M | 40 mL | $Na_2SeO_3$ solution 0.1M | 8 mL |
| $ZnCl_2$ solution 0.1M | 8 mL | $Na_2WO_4 \cdot 2H2O$ solution 0.1M | 8 mL |
| $MnCl2 \cdot 4H2O$ solution 0.1M | 8 ml | | |

Bacteria: *Clostridium autoethanogenum* used is that deposited at the German Resource Centre for Biological Material (DSMZ) and allocated the accession numbers DSMZ 19630.

Sampling and Analytical Procedures

Media samples were taken from the bioreactor at regular intervals. Each time the media was sampled care was taken to ensure that no gas was allowed to enter into or escape from the reactor.

To determine the cell density in the fermentation, the absorbance of the samples was measured at 600 nm (spectrophotometer) and the dry mass determined by extrapolation ($OD_{600}$).

HPLC:

HPLC System Agilent 1100 Series. Mobile Phase: 0.0025N Sulfuric Acid. Flow and pressure: 0.800 mL/min. Column: Alltech IOA; Catalog #9648, 150×6.5 mm, particle size 5 Temperature of column: 60° C. Detector: Refractive Index. Temperature of detector: 45° C.

Method for Sample Preparation:

400 µl of sample and 50 µL of 0.15M $ZnSO_4$ and 50 µL of 0.15M $Ba(OH)_2$ are loaded into an Eppendorf tube. The tubes are centrifuged for 10 min. at 12,000 rpm, 4° C. 200 µL of the supernatant are transferred into an HPLC vial, and 5 µL are injected into the HPLC instrument.

Headspace Analysis:

Measurements were carried out on a Varian CP-4900 micro GC with two installed channels. Channel 1 was a 10 m Molsieve column running at 70° C., 200 kPa argon and a backflush time of 4.2 s, while channel 2 was a 10 m PPQ column running at 90° C., 150 kPa helium and no backflush. The injector temperature for both channels was 70° C. Runtimes were set to 120 s, but all peaks of interest would usually elute before 100 s.

Bioreactor:

A novel, liquid circulated loop bioreactor with a working volume of 71 L was used for the fermentation of a gaseous substrate comprising CO (See FIG. 6 for a simplified schematic). The bioreactor comprises:

- A 200 mm ID vertical cylindrical riser, 3000 mm high, with a 1500 mm removable section where various types of packing may be situated.
- 2210 mm up the riser, and 170 mm above the top of the packing section, liquid is taken off through a flange into a 75 mm ID flexible hose, which attaches to a 75 mm ID stainless steel down-corner section. The heating jacket, instrument and dosing ports are situated on this section.
- The bottom of the downcomer feeds into a speed controlled centrifugal pump with a nominal flow range of 160 to 420 L/min.
- The pump outlet feeds horizontally into the bottom of the riser through a 50 mm ID stainless pipe. The flow is directed such that it creates a swirling effect in the bottom section of the riser.
- Gas enters the reactor through a large, cylindrical fine bubble diffuser (63 mm OD×350 mm), which sits vertically at the bottom of the riser. Shear from the tangential liquid flow helps to create fine bubbles.

Example 1

The removable section of the bioreactor riser was filled with ceramic monolithic packing comprising 5×5 mm square channels and a packing density of 18 cpsi. The voidage of this packing is 0.65, bringing the working volume of the reactor down from 87.5 L to 71 L.

120 mL of 85% $H_3PO_4$ was added to 80 L of solution A. The pH of the media was adjusted to 5.3 with concentrated ammonium hydroxide (28%). 800 mL of solution B (B vitamins) was added, followed by 3.14 g (0.25 mM) of cysteine. Without delay, the solution was pumped into the reactor, heated to 37° C. and degassed with nitrogen overnight with the liquid pump on. The 0.1 mol/L stock metal solutions (C) were added sequentially into a septum port on the liquid loop section.

Prior to inoculation, the gas was switched to steel mill off-gas comprising 2% H2, 30% N2, 47% CO, 21% CO2. An actively growing *Clostridium autoethanogenum* culture was inoculated into the loop reactor at a level of approximately 10% (v/v). Na2S solution (0.2M) was added at a rate of approx 5 ml/hour, increasing to approximately 30 mL/hour by the end of the run. 100 mL doses of solution B were added at day 2.2 and 2.9.

Acetate was kept reasonably constant throughout the run by regulating the amount of CO fed to the reactor, increasing both the feed gas flow and liquid pump rate as the culture grew, and using pH trends as an indicator of acetate production or consumption.

Figure 7:
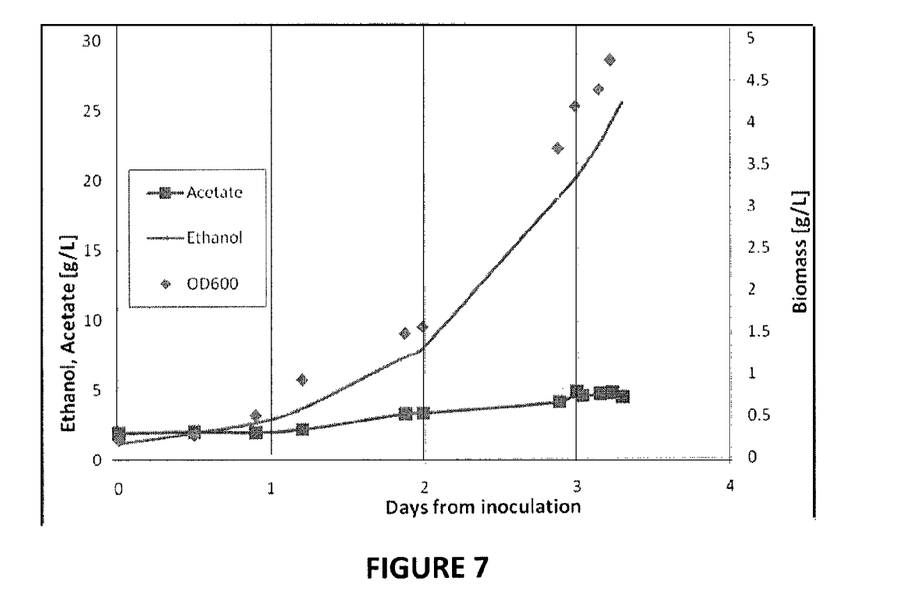
FIG. 7 shows metabolite production and microbial growth in the fermentation of a substrate comprising CO in a bioreactor comprising a gas/liquid contact module comprising multiple channels.

Results:

FIG. 7 shows a time profile of the metabolites and biomass in the reactor. After a short lag phase (0.5 days), the bacteria grew at an exponential rate ($\mu=1$) for 2.5 days until a limited supply of gas caused the premature end of the run. 25 g/L of ethanol accumulated in the broth. Ethanol productivity peaked at 20 g/L/day, with the high gas flow rates used, approximately 10% of the ethanol produced would have been stripped off in the exhaust gas toward the end of the run, but this was not quantitatively measured.

Uptake of CO reached a maximum of 5.0 mol/L/day. A measure of the mass transfer performance of the reactor ($k_L A$), was calculated from the uptake rate and solubility of CO at the temperature and pressure of the reactor. The calculation assumes that the major resistance to transfer is through the gas-liquid interface, i.e. liquid concentration of CO approximates zero. The centrifugal pump rate was increased throughout the fermentation from 400 to 850 rpm. The transfer performance climbed as gas flowrate, ethanol concentration and pump rates were all increased throughout the run, reaching a max of 0.14 $s^{-1}$.

The loop reactor comprising a channelled module can successfully grow *C. autoethanogenum*, with no signs of detriment due to running through a centrifugal pump at up to 850 rpm, or variations in gas-liquid mass transfer throughout the reactor. The mass transfer performance was very good, achieving a $k_L A$ of 0.14 $s^{-1}$, without the need for gas recycle.

Example 2

The removable section of the bioreactor riser was filled Sulzer Mellapak™ structured packing. The voidage of this packing is 0.95, making negligible impact on the reactor volume.

Gas chromatography was used to compare the input and output concentrations of gas, which was combined with mass flow controller data on the inflow to determine the gas uptake rates. HPLC was used to determine metabolite concentrations.

120 mL of 85% $H_3PO_4$ was added to 80 L of solution A. The pH of the media was adjusted to 5.3 with concentrated ammonium hydroxide (28%). 800 mL of solution B (B vitamins) was added, followed by 3.14 g (0.25 mM) of cysteine. Without delay, the solution was pumped into the reactor, heated to 37° C. and degassed with nitrogen overnight with the liquid pump on. The 0.1 mol/L stock metal solutions (C) were added sequentially into a septum port on the liquid loop section.

Prior to inoculation, the gas was switched to steel mill off-gas comprising 2% H2, 30% N2, 47% CO, 21% CO2. An actively growing *Clostridium autoethanogenum* culture was inoculated into the loop reactor at a level of approximately 10% (v/v). Na2S solution (0.2M) was added at a rate of approx 5 ml/hour, increasing to approximately 30 mL/hour by the end of the run.

Acetate was kept reasonably constant throughout the run by regulating the amount of CO fed to the reactor, increasing both the feed gas flow and liquid pump rate as the culture grew, and using pH trends as an indicator of acetate production or consumption.

Figure 8:
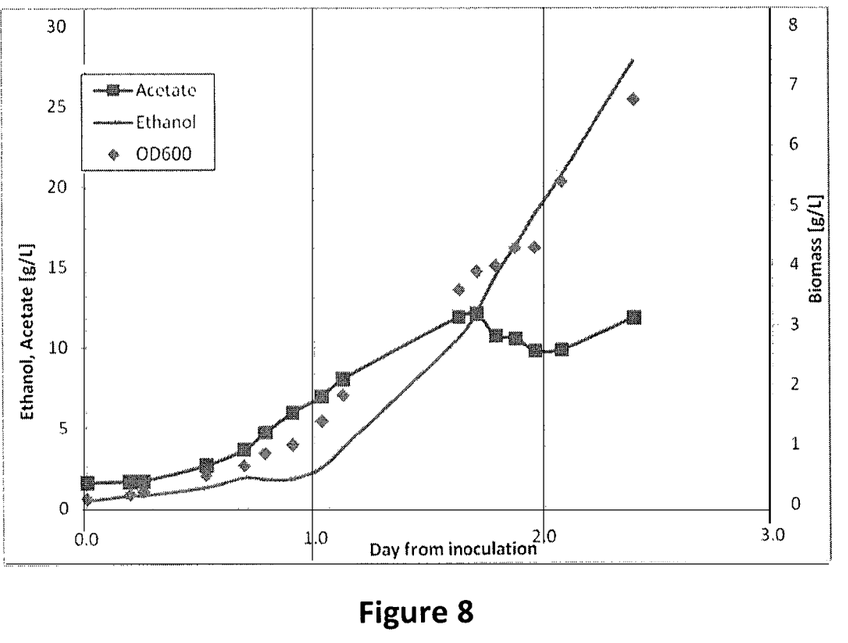
FIG. 8 shows metabolite production and microbial growth in the fermentation of a substrate comprising CO in a bioreactor comprising a gas/liquid contact module.

Results:

FIG. 8 shows a time profile of the metabolites and biomass in the reactor. The bacteria grew from inoculation at a fast exponential rate ($\mu$=2.1 day$^{-1}$), without lag. At day 2.4, a reactor fault caused the premature end of the run. 25 g/L of ethanol and 11.7 g/L acetate had accumulated in the broth. Ethanol productivity peaked at 23.9 g/L/day. With the gas flow rates used, a theoretical stripping rate of approximately 2 g/L/day ethanol was calculated for conditions toward the end of the run, but this was not quantitatively measured.

Uptake of CO reached a maximum of 5.66 mol/L/day. A measure of the mass transfer performance of the reactor ($k_L A$), was calculated from the uptake rate and solubility of CO at the temperature and pressure of the reactor. The calculation assumes that the major resistance to transfer is through the gas-liquid interface, i.e. liquid concentration of CO is zero. The centrifugal pump rate was increased throughout the run from 600 to 1250 rpm. The transfer performance climbed as gas flowrate, ethanol concentration and pump rates were all increased throughout the run, reaching a max of 0.15 s$^{-1}$.

The loop reactor setup with a centrifugal pump can successfully grow *C. autoethanogenum* at this scale, with no signs of major detriment due to running through the pump at up to 1250 rpm.

The invention has been described herein with reference to certain preferred embodiments, in order to enable the reader to practice the invention without undue experimentation. Those skilled in the art will appreciate that the invention can be practiced in a large number of variations and modifications other than those specifically described. It is to be understood that the invention includes all such variations and modifications. Furthermore, titles, heading, or the like are provided to aid the reader's comprehension of this document, and should not be read as limiting the scope of the present invention. The entire disclosures of all applications, patents and publications cited herein are herein incorporated by reference.

More particularly, as will be appreciated by one of skill in the art, implementations of embodiments of the invention may include one or more additional elements. Only those elements necessary to understand the invention in its various aspects may have been shown in a particular example or in the description. However, the scope of the invention is not limited to the embodiments described and includes systems and/or methods including one or more additional steps and/or one or more substituted steps, and/or systems and/or methods omitting one or more steps.

The reference to any prior art in this specification is not, and should not be taken as, an acknowledgement or any form of suggestion that that prior art forms part of the common general knowledge in the field of endeavour in any country.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

What we claim is:

1. A process for the fermentation of a gaseous substrate comprising CO to produce one or more products the process comprising:
   a) passing the gaseous substrate and a liquid media stream to a gas/liquid contact zone of a bioreactor and provide a fermentation broth;
   b) passing the fermentation broth to a fermentation zone of the bioreactor operated at conditions to produce an effluent stream comprising products;
   c) taking a slip stream of the fermentation broth from the fermentation zone and recycling it to the gas/liquid contact zone
   d) passing the effluent stream to a separation zone operated at conditions to produce a gaseous outlet stream comprising CO and a liquid outlet stream comprising products;
   e) passing the liquid outlet stream to a second separation zone operated at conditions to produce a purified product stream comprising ethanol and a recycle liquid stream comprising liquid media; and
   f) collecting the purified product stream.

2. The process of claim 1 further comprising recycling at least a portion of the recycle stream to the gas/liquid contact zone.

3. The process of claim 1 further comprising passing the gaseous outlet stream of step (c) to a gas separation zone operated at conditions to separate the gaseous outlet stream into a recycle gas stream comprising CO and a waste stream.

4. The process of claim 3 further comprising recycling at least a portion of the recycle gas stream to the gas/liquid contact zone.

5. The process of claim 1 where the gas/liquid contact zone comprises at least one gas liquid contact module selected from the group consisting of structured packing materials, random packing materials, sieve plates and static mixers.

6. The process of claim 5 where the structured packing material comprises a monolithic structure comprising multiple parallel channels running the length of the monolith.

7. The process of claim 6 where the monolithic structure is constructed of a ceramic material.

8. The process of claim 7 where the contact module is Mellapak™.

9. The process of claim 1 where the liquid media comprises at least one carboxydotrophic micro-organism suspended in an aqueous solution further comprising nutrients.

10. The process of claim 9 where the carboxydotrophic microorganism is selected from the group consisting of *Clostridium, Moorella, Pyrococcus, Eubacterium, Desulfobacterium, Carboxydothermus, Acetogenium, Acetobacterium, Acetoanaerobium, Butyribaceterium,* and *Peptostreptococcus*.

11. The process of claim 10 where the *Clostridium* microorganism is selected from the group consisting of *Clostridium autoethanogenum, Clostridium ljungdahli, Clostridium ragsdalei,* and *Clostridium carboxydivorans*.

12. The process of claim 1 where the gaseous substrate comprises from about 15% to about 95% CO by volume.

13. The process of claim 1 where the gaseous substrate comprises from about 40% to about 70% CO by volume.

14. The process of claim 1 where the gaseous substrate further comprises $H_2$ or a combination of $CO_2$ and $H_2$.

15. The process of claim 1 where the products are selected from the group consisting of alcohols, acids and mixtures thereof.

16. The process of claim 15 where the alcohol is ethanol.

17. The process of claim 1 where the gaseous substrate comprises a gas obtained as a by-product of an industrial process selected from the group consisting of ferrous metal products manufacturing, non-ferrous products manufacturing, petroleum refining processes, gasification of biomass, gasification of coal, electric power production, carbon black production, ammonia production, methanol production and coke manufacturing.

18. The process of claim 17 where the industrial process is ferrous metal products manufacturing.

19. The process of claim 1 where the gaseous substrate is introduced into the gas/liquid contact zone by a sparger or a fine bubble diffuser.

20. The process of claim 5 where the structured packing material is constructed of corrugated sheets of a resiliently flexible material.

* * * * *